United States Patent [19]

Mesek et al.

[11] 4,388,075
[45] Jun. 14, 1983

[54] DISPOSABLE DIAPER WITH WIDE ELASTIC GATHERING MEANS FOR IMPROVED COMFORT

[75] Inventors: Frederick K. Mesek; Virginia R. Mesek, both of Oak Forest, Ill.

[73] Assignees: Johnson & Johnson Baby Products Company, New Brunswick, N.J.; Johnson & Johnson Baby Products Company, New Brunswick, N.J.

[21] Appl. No.: 119,898

[22] Filed: Feb. 8, 1980

Related U.S. Application Data

[63] Continuation-in-part of Ser. No. 1,616, Jan. 8, 1979, abandoned, and a continuation-in-part of Ser. No. 106,182, Dec. 21, 1979, Pat. No. 4,324,245, which is a continuation-in-part of Ser. No. 862,309, Dec. 20, 1977, abandoned.

[51] Int. Cl.³ .............................................. A41B 13/02
[52] U.S. Cl. ..................................... 604/385; 428/913
[58] Field of Search ............... 128/284, 287; 428/913; 604/358, 381, 385

[56] References Cited

U.S. PATENT DOCUMENTS

| | | | |
|---|---|---|---|
| 3,860,003 | 1/1975 | Buell | 128/287 |
| 3,860,004 | 1/1975 | Nystrand | 128/287 |
| 3,987,794 | 10/1976 | Schaar | 128/284 |
| 3,995,640 | 12/1976 | Schaar | 128/284 |
| 4,050,462 | 9/1977 | Woon et al. | 128/287 |
| 4,324,245 | 4/1982 | Mesek et al. | 128/287 |

*Primary Examiner*—James J. Bell
*Attorney, Agent, or Firm*—Martha A. Michaels; Martha A. Michaels

[57] ABSTRACT

A disposable diaper having a gathering means adjacent at least one edge of the absorbent panel is disclosed. In a preferred embodiment, the gathering means is defined by an elastic member having a width dimension of at least ⅜" and a width-to-thickness ratio of at least 100, which provides improved body conformity without undue application of pressure upon the skin of the wearer. The inventive concept in its broadest sense relates to the distribution of the force of gathering means over larger areas to minimize skin irritation. In certain embodiments of the present invention, our improved diaper may have a pleasing ruffled effect at the diaper edge.

26 Claims, 12 Drawing Figures

DISPOSABLE DIAPER WITH WIDE ELASTIC GATHERING MEANS FOR IMPROVED COMFORT

BACKGROUND OF THE INVENTION

The present application is a continuation-in-part application of our co-pending patent application Ser. No. 1,616, filed Jan. 8, 1979 now abandoned, and is a continuation-in-part application of co-pending patent application 106,182 filed Dec. 21, 1979, now issued U.S. Pat. No. 4,324,245 which in turn is a continuation of Ser. No. 862,309, Dec. 20, 1977, now abandoned.

The present invention relates to improvements in disposable diapers which enable the diaper to closely conform to the torso of the wearer without applying undue pressure upon the skin of the wearer.

Recently, disposable diapers have been introduced into the marketplace which have a narrow but relatively thick strip of elastic at each side thereof, so as to gather the side margins of the diaper in a manner similar to that of conventional moisture-impermeable panties. Such diapers are made generally in accordance with the teachings of U.S. Pat. No. 3,860,003. In order for the elastic members to be effective in such diapers, it is necessary that the elastic members be spaced relatively far from the side marginal edges of the absorbent panel of the diaper, and for the elastic members to be associated with thin, highly flexible facing and backing layers. As a result, when such diapers are placed upon a baby, the narrow but relatively thick elastic members cause a narrow band of the facing layer to bear against the baby's skin. This results in a high degree of stress concentration that may cause pinching and irritation of the baby's skin.

In U.S. Pat. No. 4,050,462, a disposable diaper is disclosed having elastically extendable means which longitudinally contract the crotch section of the diaper. The elastically extendable means are located sufficiently close to the edge of the absorbent batt in the crotch region to form a plurality of gross rugosities along the length of the crotch region, meant to reduce the constriction force applied to the skin. However, excessive pressure may be applied to the skin of the wearer due to the high modulus elastic necessary to gather the panel across the entire width of the crotch region.

The problems attributable to the unduly high compressive force caused by such narrow but relatively thick elastic strips of the prior art diapers mentioned above are particularly acute when the baby has voided and the diaper is wet. Because the backing and facing layers are so highly flexible, when the diaper is wet and conditions are present tending to cause hydration of the baby's skin, the narrow elastic members often cause the facing layer to press against the skin with sufficient force to injure the skin.

SUMMARY OF THE INVENTION

The disposable diapers of the present invention include gathering means adjacent at least one edge of the absorbent panel of the diaper. In one embodiment, gathering means are located adjacent the two side edges of the diaper. In addition, gathering means may be located adjacent one or both end edges of the diapers. The gathering means of the present invention provide improved body conformity of the diaper without undue application of pressure upon the skin of the wearer.

Diapers constructed in accordance with the present invention have several unexpected advantages over the prior art and in particular, over the diapers of the type disclosed in U.S. Pat. No. 3,860,003. By the use of the improved gathering means in accordance with the present invention, the force applied to gather the leg opening of the diaper, pressing against the skin of the wearer through the facing layer, is distributed over a larger area, resulting in improved comfort for the wearer. In addition, because of the relatively large area of facing material engaging the wearer's skin, improved gasketing around the thighs of the wearer is achieved thereby minimizing fluid leakage from the diaper.

In the preferred embodiment of the present invention, the gathering means have a width of at least about ⅜", preferably a width of at least ½", and more preferably a width of from about ¾" to about 1¼". The width-to-thickness ratio should be at least about 100 and preferably about 500 to about 1000.

The elastic members defining the gathering means may be secured to the facing layer and/or the backing layer, and may be secured by two or more spaced lines of attachment cooperating with one another to provide visibly distinct separate lines of simulated stitching, providing further improved gasketing about the leg of the wearer, as well as a pleasing appearance.

The elastic members of the present invention also improve the ease of manufacture of the disposable diapers. The wider elastic members are easier to manipulate and control during the manufacturing process. In addition, alignment of the elastic securing means to the elastic member may become less critical because of the increased width dimension of the elastic member and because the securing means may contact the elastic member at any location across its width.

DESCRIPTION OF THE PREFERRED EMBODIMENTS

For a disposable diaper of the present invention, the gathering means is a readily stretchable, elastic, preferably thermoplastic member of substantial width that possesses a certain minimum elastic recovery.

The term "elastic", as used herein refers to sheets, films, ribbons and the like which have a recovery of at least 90 percent, when elongated at least 10 percent of their yield point and measured in accordance with the following formula:

$$\text{Percent Retraction} = \frac{L_e - L_i}{L_e - L_o} \times 100$$

where
- $L_o$ = original length of sample
- $L_e$ = fully extended length
- $L_i$ = length of sample measured 3 seconds after released from extended length.

The thickness of the elastic members is generally 10 mils or less, and preferably about 0.5 to about 5 mils. The elastic members have an extensibility to rupture of at least about 300 percent, preferably about 400 to about 1000 percent and a recovery at 50 percent elongation of at least about 75 percent, and preferably at least about 80 percent. For ease of stretchability, the modulus of elasticity of the elastic member at 50 percent elongation should not exceed about 2000 pounds per square inch, and preferably is about 100 to about 200 pounds per square inch.

Figure 1:
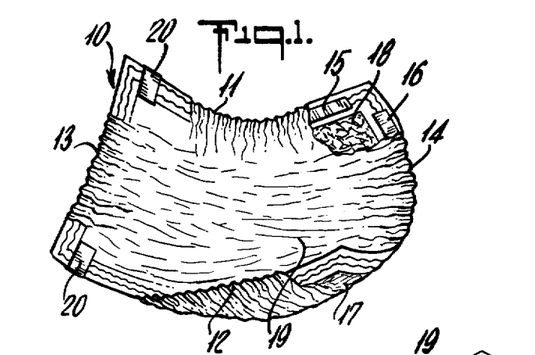
FIG. 1 is a perspective view illustrating a disposable diaper embodying the present invention with a portion broken away to show interior detail.

Referring to FIG. 1, disposable diaper 10 illustrating one embodiment of the present invention is provided with marginal longitudinal gathering means in opposite side margins 11 and 12 adapted to provide enhanced fit and gasketing about the baby's thighs. Additionally, optional transverse gathering means are provided in end margins 13 and 14 for enhanced fit about the baby's waist. The gathering means in each side margin comprises an elastic member, such as elastic member 15 in side margin 11 having a width of ⅜" and a width-to-thickness ratio of at least 100. The optional transverse gathering means in the end margins of diaper 10 can be a similar elastic member such as member 16 in end margin 14. Diaper 10 additionally includes first outer layer or backing 17 made of a moisture-impervious web, a generally rectangular absorbent panel 18 positioned in superposed relationship with respect to the backing, and second outer layer or facing 19 made of a moisture-pervious or permeable web and positioned in superposed relationship with respect to absorbent panel 18. For securement about a baby, diaper 10 is provided with pressure-sensitive adhesive tape tabs 20 and 21. The longitudinal gathering means are generally parallel to the longitudinal side margins of panel 18, and when the gathering means are in a relaxed state, diaper 10 assumes a boat-like configuration as shown in FIG. 1, with side margins 11 and 12 having a reduced length.

Figure 2:
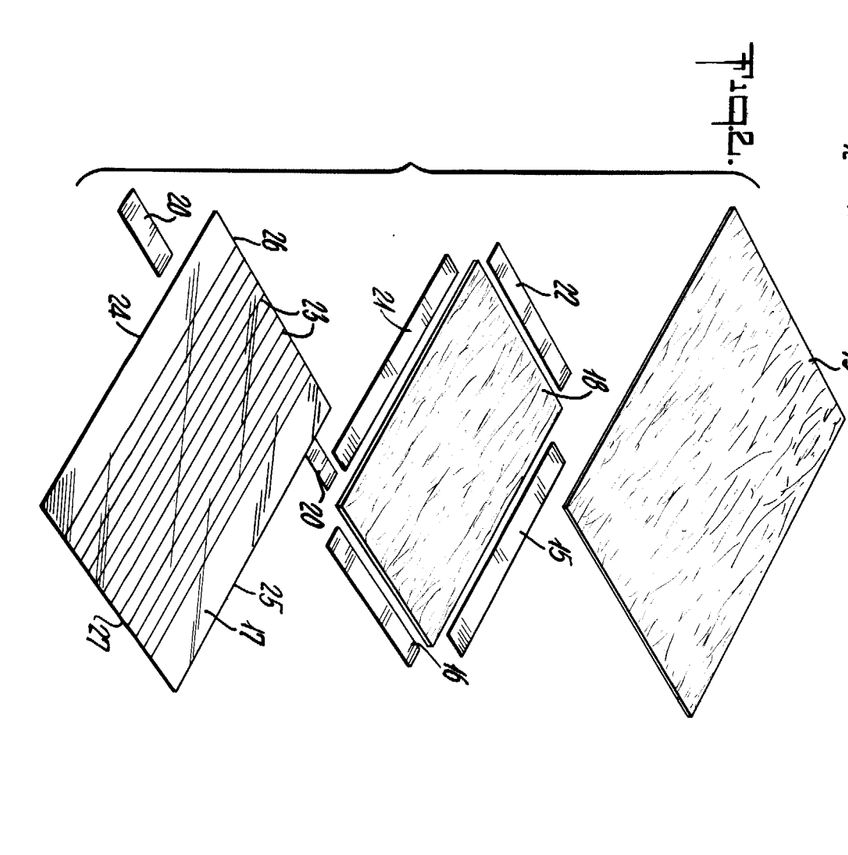
FIG. 2 is an exploded perspective view showing relative positioning of diaper elements during manufacture of the diaper depicted in FIG. 1.

The individual components of disposable diaper 10 are illustrated in FIG. 2. Absorbent panel 18 is superposed over backing 17 and is secured thereto by a series of glue lines 23 deposited on backing 17. Absorbent panel 18 is of smaller area than backing 17 and, when substantially centered on backing 17, is spaced from longitudinal sides 24 and 25 as well as transverse sides or ends 26 and 27 and thereby defines the side and end marginal portions of diaper 10. Absorbent panel 18 is flanked on all four sides thereof by elastic film members 15, 16, 21 and 22 which, in an extended state, are secured to backing 17 by means of an elastic or inelastic adhesive, heat sealing, sonic sealing described below, or in any other convenient manner.

In securing the elastic film members in place, they should be secured across substantially the entire width of the member, i.e., at least a width of ⅜". For example, if a ⅜" wide elastic film member is used, it could be secured to the backing, while the member is in a stretched state, by applying adhesive across the full width of the member and intermittently along the length of the member. In another embodiment if a member wider than ⅜" is used, it can be secured to the backing, while the member is in a stretched state, by a pair of glue lines extending longitudinally of the member provided the glue lines are spaced at least ⅜" apart. Therefore, in accordance with the present invention, the gathering means is effective over a width of at least ⅜"; i.e., its area of gathering has a width dimension of ⅜" or greater.

Moisture-pervious facing 19 is superposed over absorbent panel 18, is larger in area than panel 18, and is secured to backing 17, usually by means of the exposed end portions of glue lines 23. However, other securement means can be utilized, if desired. Facing 19 may also be secured to elastic film members 15, 16, 21 and 22 in a manner similar to the securement thereof to backing 17.

As stated above, the elastic film members may be conveniently secured in place ultrasonically, such as by the use of apparatus of the type that is commercially available from Branson Instruments, Inc. of Stanford, Connecticut. Such apparatus conventionally includes an anvil and a horn that are positioned in juxtaposed relationship to one another, and the parts to be joined are inserted therebetween. The horn is energized to transmit vibrations in the ultrasonic frequency range into the parts to be joined. In the present instance, the elastic film members are enlongated between backing layer 17 and facing layer 19, and the layers placed between a horn which coacts with an anvil which moves in registration with the product to provide a plurality of spaced rows of simulated stitching. In this regard, the anvil of the ultrasonic sealing apparatus preferably is provided with a plurality of spaced land areas so that the stretch elastic film members are secured in place by a plurality of spaced securement zones. Spaced securement zones are also provided when the method of securement is heat sealing or inelastic adhesive. When elastic adhesive is used, lines of attachment may be continuous.

Figure 3:
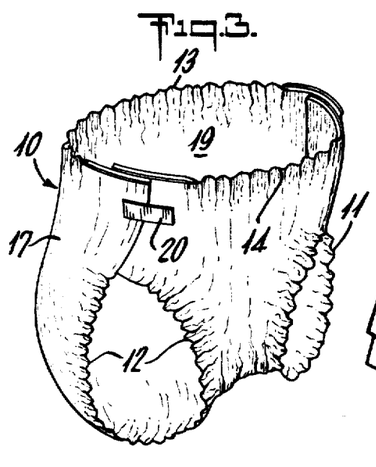
FIG. 3 is a perspective view of the diaper of FIG. 1 illustrating diaper configuration when applied about a baby.

The configuration that disposable diaper 10 assumes when applied to a baby is illustrated in FIG. 3. Partially-extended diaper side margins 11 and 12 provide a comfortable yet positive seal about the baby's thighs that readily accommodates leg movements of the baby, while optional elastic members in diaper end margins 13 and 14 assure good fit about the baby's waist.

Figure 4:
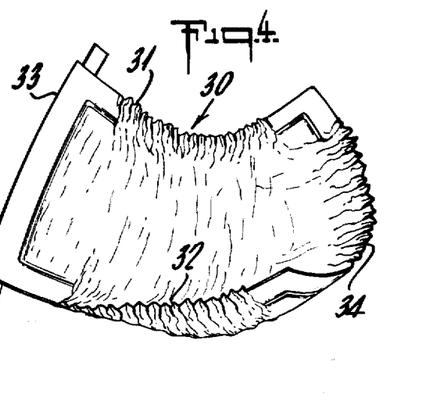
FIG. 4 is a perspective view showing another embodiment of the disposable diaper of this invention.

FIG. 4 shows disposable diaper 30 that is similar to disposable diaper 10 but lacks the optional elastic member in diaper end margin 33. In the embodiment exemplified by FIG. 4 the elastic member in diaper end margin 34 is similar to elastic member 16 in FIG. 1 and performs in the same manner. The construction of diaper side margins 31 and 32 is substantially the same as in diaper side margins 11 and 12.

Figure 5:
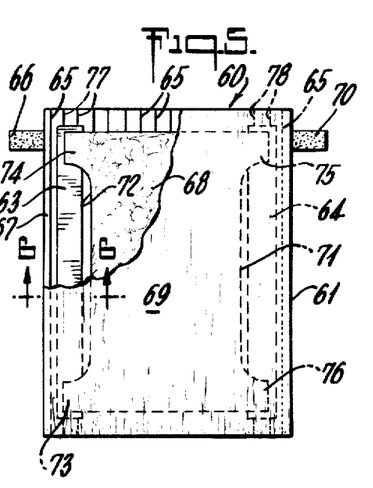
FIG. 5 is a plan view of yet another embodiment of a disposable diaper of this invention with a portion broken away to show interior detail.
Figure 6:
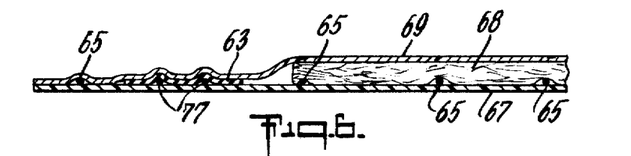
FIG. 6 is an enlarged partial cross-section of FIG. 5 taken along lines 6—6.

In the embodiment illustrated by FIG. 5, disposable diaper 60 is provided with absorbent panel 68 having curvilinear side cut-outs 71 and 72 and sandwiched between facing 69 and backing 67. Glue lines 65 serve to secure panel 68 and facing 69 to backing 67. Elastic members 63 and 64 are situated in generally rectilinear diaper side margins 62 and 61. Elastic members 63 and 64 extend substantially the entire length of diaper side margins 62 and 61, respectively, and are secured to backing 67 by spaced outer glue lines 77 and 78. Glue lines 77 are illustrated in cross-section in FIG. 6. The glue lines 77 and 78 provide separate lines of attachment and gathering or simulated gathered stitching which in turn create separate lines of gasketing of the puckered facing against the legs of the wearer. Protruding ears 73, 74, 75 and 76 of absorbent panel 68 overlap substantially the entire width of the respective elastic members 63 and 64 and provide additional absorbent capacity which can be readily utilized by building into absorbent panel 68 appropriate capillary transport means. Adhesive tape tab means 66 and 70 provide means for securing diaper 60 about a baby.

Figure 7:
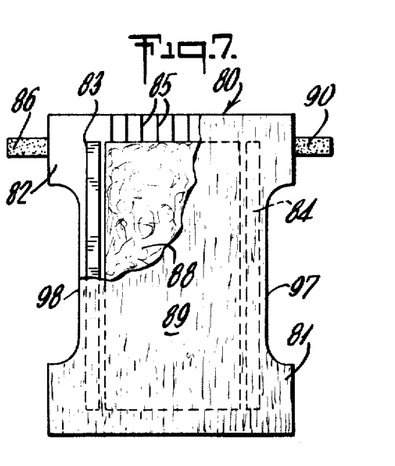
FIG. 7 is a plan view of a still further embodiment of a disposable diaper of this invention with a portion broken away to show interior detail.

In the embodiment of FIG. 7, disposable diaper 80 is provided with substantially rectangular absorbent panel 88 having generally rectilinear sides, sandwiched between backing 87 and facing 89, and together with backing 87 and facing 89 defining diaper side margins 81 and 82. Curvilinear cut-outs 97 and 98 are provided in the respective central portions of margins 81 and 82 for further fit enhancement. Prestretched elastic members 83 and 84 are positioned in respective margins 82 and 81 and are secured to backing 87 and/or facing 89 along the longitudinal sides of absorbent panel 88. Glue lines 85 secure facing 89 and absorbent panel 88 to backing 87, and adhesive tape tabs 86 and 90 provide diaper securement means.

Figure 8:
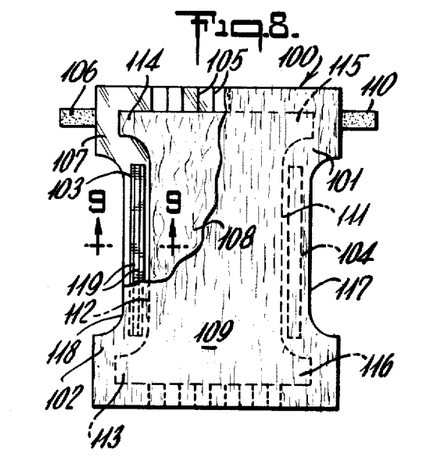
FIG. 8 is a plan view of an additional embodiment of a disposable diaper of this invention with a portion broken away to show interior detail.
Figure 9:
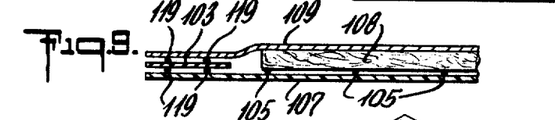
FIG. 9 is a cross-sectional view of the diaper of FIG. 8 taken along lines 9—9, in which the spacing of the backing layer, facing layer, and panel have been exaggerated to clarify the illustration of the glue lines.

Yet another embodiment of a disposable diaper according to the present invention is shown in FIGS. 8 and 9 where disposable diaper 100 is provided with shaped absorbent panel 108 having curvilinear cut-outs 111 and 112 and centrally juxtaposed between backing 107 and facing 109. Both panel 108 and facing 109 are secured to backing 107 by a plurality of longitudinally extending glue lines 105. Curvilinear cut-outs 117 and 118, similar in configuration but of smaller size than cut-outs 111 and 112, are provided in the side portions of facing 109 and backing 107 that form diaper side marginal portions 101 and 102, respectively, so that margin cut-out 117 subtends panel cut-out 111 and margin cut-out 118 subtends panel cut-out 112. Elastic member 103 is positioned in diaper side marginal portions 102 between protruding ears 113 and 114 of absorbent panel 108 and is secured to facing 109 and backing 107. In a similar manner, elastic member 104 is positioned in diaper side marginal portion 101 between protruding ears 115 and 116 of absorbent panel 108 and is secured to facing 109 and backing 107 by spaced lines of attachment 119. Facing 109 and backing 107 are not secured to each other in the side marginal portion between the gathering means and the longitudinal side edge of the diaper, creating a soft, ruffly side edge of the diaper, illustrated in FIG. 12. Diaper securement means are provided by adhesive tape tabs 106 and 110.

Figure 12:
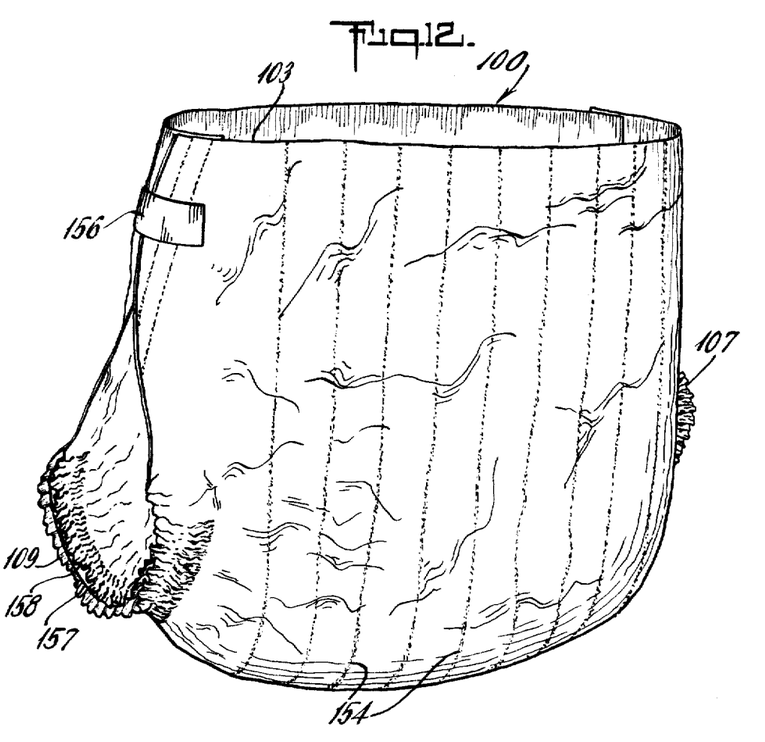
FIG. 12 is an enlarged perspective view showing the embodiment of FIG. 8 and in the configuration it assumes when applied to a baby.

Diaper 100 is illustrated in FIG. 12 in the configuration it assumes when applied to a baby. The elastic member 103, as well as the facing 109 and backing 107 layers, extend outboard of the lines of attachment and all three assume independently gathered formations, creating the soft, ruffly side edges 154 and 155 of the diaper.

The spaced lines of attachment of the elastic member to the facing layer create plural lines of sealing about the leg of the wearer aided by the puckering or gathering of the facing layer adjacent each line of attachment securing the elastic member to the facing layer, thereby providing improved liquid containment at the leg opening.

Figure 10:
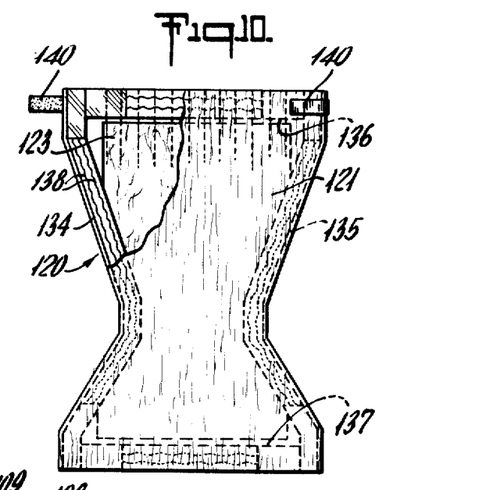
FIG. 10 is a plan view of another embodiment of the disposable diaper of the present invention.
Figure 11:
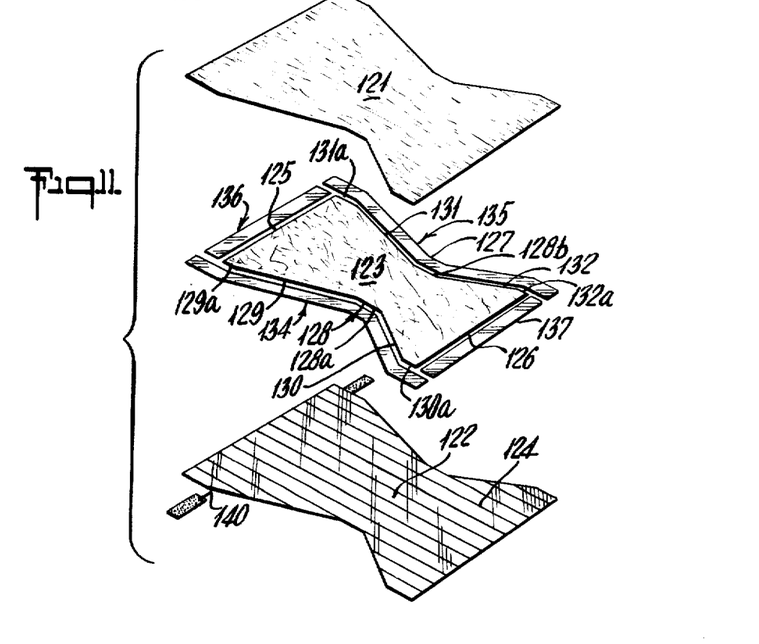
FIG. 11 is an exploded perspective view of the elements of the diaper illustrated in FIG. 10.

Referring now to FIGS. 10 and 11, a still further embodiment of the invention is illustrated in its entirety at 120, and includes a first outer layer 121 in the form of a moisture-pervious facing, a second outer layer 122 in the form of a moisture-impervious backing, a third layer 123 in the form of an absorbent panel sandwiched therebetween, and adhesive tape tabs 140. Outer layers 121 and 122 have the same outer dimensions and are coterminous with one another. Panel 123 has an external configuration similar to layers 121 and 122, and is smaller than the centered relative to layers 121 and 122. Parallel glue lines 124 on backing 122 secure the panel to the backing, and the outermost glue lines (and the ends of the intermediate glue lines) secure the portions of layers 121 and 122 that extend beyond panel 123 to one another.

The end portions 125 and 126 of panel 123 are generally equal in width and are wider than the panel mid-portion 127. For improved fit, the narrowest part 128 of the panel mid-portion is offset toward panel end portion 126, the portion that is adapted to be placed in front of the infant. Panel portion 128 is of relatively short length and is formed between parallel side edges 128a and 128b. Panel side edges 129, 130, 131 and 132 flare outwardly from the ends of edges 128a and 128b and terminate in end portion 129a parallel with end portion 131a and end portion 130a parallel with end portion 132a. In a most preferred embodiment of the invention, edges 129 and 131 are disposed at an angle of 25° and edges 130 and 132 are disposed at an angle of 35° so that the included angle between edges 129 and 130 and edges 131 and 132 is 120°.

As with the previously described embodiments, diaper 120 includes gathering means 134 and 135 at opposite sides of the diaper, and optional gathering means 136 and 137 at opposite ends of the diaper. The illustrated gathering means are in the form of elongated elastic members that are secured in a stretched condition to layers 121 and/or 122. The securement means may take the form of spaced lines of attachment 138. Adhesive tape tabs 140 are provided to secure the diaper 120 about the torso of a baby.

Elastic film members suitable as gathering means for the diapers contemplated herein can be extruded to the desired thickness utilizing unvulcanized, thermoplastic compositions which are made up of an elastomeric component and an optional compatible modifier which is a thermoplastic polymer of a relatively low molecular weight but solid at ambient temperature.

Illustrative of the elastomeric components suitable for present purposes are block copolymers which comprise terminal thermoplastic polymer blocks and at least one non-terminal or intermediate elastomeric polymer block. Block copolymers of this general type may be prepared using a step-wise polymerization initiator, e.g., an organolithium compound. Such block polymerization techniques are well known in the art.

The elastomeric component can be linear or radial $A^1$-B-$A^2$ block copolymers or mixtures thereof with simple $A^1$-B block copolymers where $A^1$ and $A^2$ can be alike or different and represent a thermoplastic polymer block, such as poly(vinyl arene) block, and B represents an elastomeric polymer block such as a conjugated diene or a lower (i.e., $C_1$-$C_4$)alkene. The modifier component is a low molecular wieght thermoplastic polymer having an average molecular weight of about 500 to about 7,500 and is present in the composition in an amount of about zero to about 200 parts by weight per 100 parts by weight of the elastomeric component.

A preferred thermoplastic film composition for the elastic film members comprises an elastomeric component which contains, as a major constituent thereof, an unvulcanized linear block copolymer of the general configuration $A^1$—B—$A^2$ wherein $A^1$, $A^2$ and B have the same meaning as hereinabove. In these block copolymers, the A-blocks are derived from styrene or styrene homologues, and the B blocks are derived from conjugated dienes or lower alkenes. The thermoplastic polymer modifier is compatible with the elastomeric component and associates principally with the thermoplastic terminal blocks of the aforesaid unvulcanized block copolymer. The thermoplastic polymer modifier preferably has an average molecular weight of about 1000 to about 3000, and is present in the film composition in an amount of about 80 to about 200 parts by weight per 100 parts by weight of the elastomeric component.

The preferred $A^1$-B-$A^2$ block copolymers have A-blocks derived, i.e., polymerized or copolymerized, from styrene or styrene homologues; and B-blocks derived from conjugated dienes, such as isoprene or butadiene, or from lower alkenes, such as ethylene and butylene. Small proportions of other monomers also may enter into the block copolymers themselves. The individual A-blocks can have an average molecular weight of at least about 6,000, preferably in the range of about 8,000–30,000, and the A-blocks constitute about 5–50 percent, preferably about 10–30 percent, by weight of the block copolymer. The average molecular weight of the B-blocks for linear $A^1$-B-$A^2$ block copolymers preferably is in the range of about 45,000–180,000 and that of the linear copolymer itself, preferably is in the range of about 75,000–200,000. The average molecular weight of the radial $A^1$-B-$A^2$ block copolymers preferably is in the range of about 125,000–400,000. The term "Linear block copolymer" (or copolymers) includes branched $A^1$-B-$A^2$ copolymers as well as unbranched $A^1$-B-$A^2$ copolymers.

The radial $A^1$-B-$A^2$ copolymers useful for manufacture of elastic members for diapers of this invention are of the type described in U.S. Pat. No. 3,281,383 to Zelinski et al. and conform to the following general formula: $(A\text{-}B\text{-})_n X$, and wherein A is a thermoplastic block polymerized from styrene or styrene homologues, B is an elastomeric block derived from conjugated dienes or lower alkenes, as indicated above, X is an organic or inorganic connecting molecule with a functionality of about 2 to 4 as described in U.S. Pat. No. 3,281,383, or possibly with a higher functionality as described in the article entitled "New Rubber is Backed by Stars" appearing on Page 35 of the June 11, 1975 issue of *Chemical Week*. As used hereinabove, "n" has a value corresponding to the functionality of X.

Another suitable elastomeric component is elastomers wherein the sheet material contains thermoplastic rubber and amorphous polypropylene. The thermoplastic rubbers are block copolymers having blocks of polybutadiene or polyisoprene, and blocks of polystyrene. A review article discussing these materials is "Structure And Properties Of Block Polymers And Multi-phase Polymer Systems: An Overview Of Present Status And Future Potential", by S. L. Aggarwal, *Polymer*, Vol. 17, November 1976, pages 938-956. Two representative types of thermoplastic rubbers are the linear block copolymers (A-B-A) having a mid-block of polybutadiene or polyisoprene and endblocks of polystyrene, and the "star" or "radial" block copolymers having from 4 to 20 "arms" connected to a common center. Each arm is an A-B block copolymer, the inner portion being polybutadiene or polyisoprene, with the outer portion being polystyrene.

The typical thermoplastic rubber contains discrete polystyrene domains in a rubbery matrix. Apparently the polystyrene domains act in a manner analogous to conventional chemical cross links. The resulting rubber acts as though it has been vulcanized, even though no chemical crosslinks are present.

When the thermoplastic rubber is heated to about 200°0 F., the polystyrene domains begin to soften, and at temperatures of the order of 300° F. to 400° F., the thermoplastic rubbers can be melt processed by mechanical working in a manner analogous to conventional thermoplastic compositions. Upon cooling, the discrete polystyrene domains are reformed, and the material again exhibits rubbery elastomeric properties.

While thermoplastic rubbers can be processed in ways analogous to those used for conventional thermoplastic polymers, for the reasons discussed above, it has been found to be impracticably difficult to extrude pure thermoplastic rubber into thin films.

The material that is used to improve the processability of thermoplastic rubber, while still retaining the characteristic rubbery properties of the rubber, is amorphous polypropylene. Amorphous polypropylene is a known material. It is essentially atactic polypropylene having an isotactic content of not more than about 20 weight percent, and preferably not more than about 10 weight percent.

The amorphous polypropylene is employed in an amount sufficient to improve the processability of the thermoplastic rubber when extruding thin films or sheets. Such improvement is evidenced by the ability to draw down extruded webs of the rubber/amorphous polypropylene mixture to thereby produce sheets or films having thicknesses less than the die gap. Further, the pressure in the extruder and die is greatly reduced, which permits more economical operation. The exact minimum amount of amorphous polypropylene varies somewhat from case to case, but it is usually of the order of about 10 weight percent, based on weight of rubber plus amorphous polypropylene, although the proportion may be as low as about 5 weight percent (on the same basis) in some cases. The upper limit of polypropylene will also vary from case to case, depending on the nature of the ingredients and the use intended for the product. At proportions above about 35 weight percent (on the same basis), a significant reduction in the characteristic rubbery elastomeric properties of the product begins to occur. This may be acceptable for some uses, and not for others. Thus, the upper limit of amorphous polypropylene would be that point at which the product still retains significant rubbery elastomeric characteristics.

Other conventional materials, employed in the usual amounts, can be employed in the mixture for their known purposes. Such materials include pigments, anti-blocking agents, stabilizers, anti-oxidants, ultraviolet stabilizers, bonding aid, and the like.

The preferred elastic film members are highly thermoplastic and, though elastomeric, are unlike rubber in that the film exhibits a relatively sharp melting point and is capable of being heat shaped. Also, the elastic members can form permanent heat seals to substrates such as non-woven fabrics or the like, at relatively low heat-sealing peak temperatures, generally not above about 350° F. The members are highly elastic and hve a relatively low rubber modulus, i.e., they exhibit in at least one direction an elastic recovery from 50 percent stretch to at least 75 percent, preferably at least about 80 percent, and a 50 percent rubber modulus of not above about 2000 pounds per square inch, preferably not above 1000 pounds per square inch at 50 percent elongation. The film members also are very flexible, extensible, and soft and normally exhibit a Gurley stiffness of about one or less at a film thickness of one mil, and an elongation to break of at least about 300 percent, preferably at least about 400 percent, in at least one direction at ambient temperatures.

Several different types of facing materials may be used for diaper facing. For example, the facing may be a non-woven web made up of a mixture of fibers consisting predominantly of inexpensive short cellulosic fibers such as wood pulp fibers or cotton linters, in amounts of about 75 percent to about 98 percent, the balance being textile length fibers such as rayon as described in U.S. Pat. No. 3,633,348 to Liloia, et al.

Non woven facing materials suitable for use in disposable diapers of this invention can have fabric weights in the range of about 0.5 to 5 oz/yd.$^2$ and densities of less than 0.15 g/cc., generally in the range of about 0.05 to about 0.1 g/cc. The dry strength of the facing sheet for a fabric having a weight of about 1.5 oz/yd.$^2$ is at least 0.15 lbs./in. of width in the machine direction and at least 0.1 lbs./in. of width in the cross direction. Such fabrics have unusually good elongation, loft, softness, and drape characteristics.

Facings may also be made of an apertured, non-woven fabric which is formed, for example, in accordance with the teachings of commonly assigned U.S. Pat. Nos. 2,862,251; 3,081,514 and 3,081,515. Briefly, such fabrics are foraminous structures wherein groups or groupings of fibers have been rearranged from a fibrous non-woven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a fibrous polyester type material can have a weight of about 0.75 oz/yd.$^2$.

In addition, facings can be formed of a non-apertured material, such as a non-woven isotropic web, or of an apertured polyolefin or polyester film having the desired moisture permeability. In all of the aforementioned facings, the material should be relatively hydrophobic so as to retard wicking within the facing.

The moisture-absorbent batt or panel of a desired shape but smaller than the facing and the backing, can be formed in accordance with the teachings of U.S. Pat. No. 3,612,055 to Mesek, et al.

A suitable backing material for the diapers embodying the present invention can be an opaque polyolefin, e.g., polyethylene, web about 0.001 inch thick. Another suitable material for this purpose is a polyethylene terephthalate web having a thickness of about 0.0005 inch.

In use, the disposable diaper is applied to the baby by laying out the diaper on a suitable flat surface and placing the baby thereon so that the waist-underlying end of the diaper is that having the fastener means. The other end of the diaper then extends downwardly between the infant's legs. Next, the downwardly extending end of the diaper is brought up between the baby's legs to a position covering the perineum and contiguous with the front portion of the baby's waist. The diaper is thereafter secured to the baby by placing the corners of the waist portion of the abdomen-covering end as far around the baby's waist as they will go and by bringing the corners of the underlying end of the diaper into an overlapping relationship with the aforementioned corners so that the diaper snugly encircles the baby's waist and provides a custom fit. The adhesive tab fasteners are then prepared for use and the diaper is secured in the desired position by simply urging the pressure-sensitive adhesive surface of the tape tab in contact with the adjacent outer surface of the opposite corner of the diaper. The applied diaper assumes a configuration such as shown in FIG. 3.

The foregoing description and the drawings are illustrative and are not to be taken as limiting. Still other variations and modifications are possible without departing from the spirit and scope of the present invention.

We claim:

1. A disposable diaper comprising: a moisture-permeable facing layer; an absorbent panel at one side of said facing layer, said absorbent panel being smaller than said facing layer so that marginal portions of the facing layer extend outwardly beyond the edges of said absorbent panel; a moisture-impervious backing layer at the side of said absorbent panel opposite said facing layer, said backing layer being larger than said absorbent panel so that marginal portions of the backing layer extend outwardly beyond the edges of said absorbent panel; means bonding said facing and backing layers to one another; gathering means adjacent to at least one edge of said absorbent panel, and means securing said gathering means to at least one of said layers, said gathering means being defined by an elastic member having a width dimension at least about ⅛" and having a width-to-thickness ratio of at least about 100 and being effective over a width of at least ¼", whereby said gathering means provides improved body conformity without undue application of pressure upon the skin of the wearer.

2. A disposable diaper as in claim 1 wherein said means securing said gathering means is provided by at least two spaced lines of attachment cooperating with one another to provide visibly distinct separate lines of simulated stitching.

3. A disposable diaper as in claim 1 wherein the gathering means adjacent to at least one edge of the absorbent panel is disposed between the facing layer and the backing layer.

4. A disposable diaper as in claim 3 wherein the gathering means disposed between the facing layer and backing layer is secured to both the facing layer and backing layer.

5. A disposable diaper as in claim 1 wherein the gathering means is defined by an elastic member having a width dimension of at least ⅜" and a width-to-thickness ratio of at least about 100.

6. A disposable diaper as in claim 5 wherein the gathering means is disposed between the facing layer and backing layer and is secured to both the facing layer and backing layer.

7. A disposable diaper as in claim 5 wherein said means securing said gathering means is provided by at least two spaced lines of attachment cooperating with one another to provide visibly distinct separate lines of simulated stitching.

8. A disposable diaper comprising: a moisture-permeable facing layer; an absorbent panel at one side of said facing layer, said absorbent panel being smaller than said facing layer so that marginal portions of the facing layer extend outwardly beyond the edges of said absorbent panel; a moisture-impervious backing layer at the side of said absorbent panel opposite said facing layer, said backing layer being larger than said absorbent panel so that marginal portions of the backing layer extend outwardly beyond the edges of said absorbent panel; means bonding said facing and backing layers to one another; gathering means adjacent to at least one edge of said absorbent panel, and means securing said gathering means to at least one of said layers, said securing means being provided by at least two spaced lines of attachment bonding said gathering means to said one layer, said spaced lines of attachment cooperating with one another to provide visibly distinct separate lines of simulated stitching at said one edge and gathering effective across at least ½".

9. A disposable diaper as in claim 8 wherein the gathering means adjacent to at least one edge of the absorbent panel is disposed between the facing layer and backing layer.

10. A disposable diaper as in claim 9 wherein the means securing said gathering means is provided by at least two spaced lines of attachment bonding said gathering means to said facing layer and at least two spaced lines of attachment bonding said gathering means to said backing layer.

11. A disposable diaper comprising: a first outer layer in the form of a moisture-impervious backing; an absorbent panel positioned in superposed relationship with respect to said backing, said panel being smaller than said backing and spaced inwardly from the sides and ends thereof; a second outer layer in the form of a moisture-pervious facing positioned in superposed relationship with respect to said panel, said facing being larger than said panel and having marginal portions thereof secured to said backing; gathering means in each side margin of the diaper, and means securing the gathering means to at least one of said layers, said gathering means being defined by an elastic member having a width dimension at least about ½" and having a width-to-thickness ratio of at least about 100 and being effective over a width of at least ½", whereby said gathering means provides improved body conformity without undue application of pressure upon the skin of the wearer.

12. A disposable diaper as in claim 11 wherein the gathering means are defined by an elastic member having a width dimension of at least ⅜" and a width-to-thickness ratio of at least about 100 and are effective over a width of at least ¾".

13. A disposable diaper as in claim 11 including gathering means disposed in at least one end margin of the diaper.

14. A disposable diaper as in claim 11 wherein the gathering means are disposed between the facing layer and the backing layer.

15. A disposable diaper as in claim 14 wherein the gathering means disposed between the facing layer and the backing layer are secured to both layers.

16. A disposable diaper as in claim 11 wherein the means securing each of said gathering means are provided by at least two spaced lines of attachment cooperating with one another to provide visibly distinct separate lines of simulated stiching.

17. A disposable diaper as in claim 11 wherein the gathering means are defined by an elastic member having a width dimension of at least ⅜" and a width-to-thickness ratio of at least about 100 and are effective over a width of at least ¾", said gathering means are disposed between the backing layer and facing layer, and the means securing said gathering means are provided by at least two spaced lines of attachment bonding said gathering means to said facing layer and at least two spaced lines of attachment bonding said gathering means to said backing layer.

18. A disposable diaper comprising: a first outer layer in the form of a moisture-impervious backing; an absorbent panel positioned in superposed relationship with respect to said backing, said panel being smaller than said backing and spaced inwardly from the sides and ends thereof; a second outer layer in the form of a moisture-pervious facing positioned in superposed relationship with respect to said panel, said facing being larger than said panel and having marginal portions thereof secured to said backing; gathering means in each side margin of the diaper, and means securing the gathering means to the facing, said gathering means being defined by an elastic member having a width dimension at least about ½" and having a width-to-thickness ratio of at least about 100 and being effective over a width of at least ½", whereby said gathering means provides improved body conformity without undue application of pressure upon the skin of the wearer, and provides improved liquid containment.

19. A disposable diaper comprising: a first outer layer in the form of a moisture-impervious backing; an absorbent panel positioned in superposed relationship with respect to said backing, said panel being smaller than said backing and spaced inwardly from the sides and ends thereof; a second outer layer in the form of a moisture-pervious facing positioned in superposed relationship with respect to said panel, said facing being larger than said panel and having marginal portions thereof secured to said backing; gathering means in at least one end margin of the diaper and means securing said gathering means to at least one of said layers, said gathering means being defined by an elastic member having a width dimension at least about ½" and having a width-to-thickness ratio of at least about 100 and being effective over a width of at least ½", whereby said gathering means provides improved body conformity without undue application of pressure upon the skin of the wearer.

20. A disposable diaper as in claim 19 wherein the gathering means is defined by an elastic member having a width dimension of at least ¾" and a width-to-thickness ratio of at least about 100 and is effective over a width of at least ¾".

21. A disposable diaper as in claim 19 wherein said means securing said gathering means is provided by at least two spaced lines of attachment cooperating with one another to provide visibly distinct separate lines of simulated stitching.

22. A disposable diaper as in claim 19 wherein the gathering means is defined by an elastic member having a width dimension of at least ¾" and a width-to-thickness ratio of at least about 100 and is effective over a width of at least ¾", gathering means is disposed between the backing layer and the facing layer, and the means securing said gathering means is provided by at least two spaced lines of attachment bonding said gathering means to said facing layer and at least two spaced lines of attachment bonding said gathering means to said backing layer.

23. A disposable diaper comprising: a first outer layer in the form of a moisture-impervious backing; an absorbent panel positioned in superposed relationship with respect to said backing, said panel being smaller than said backing so that side marginal portions of the backing extend outwardly beyond the side edges of said absorbent panel; a second outer layer in the form of a moisture-pervious facing in superposed relationship with respect to said panel, said facing being larger than said absorbent panel so that side marginal portions of the facing extend outwardly beyond the side edges of said absorbent panel; gathering means disposed in said side marginal portions between said facing and said backing and inwardly of the side edges of the diaper, said gathering means being defined by an elastic member having a width dimension at least about ¼" and having a width-to-thickness ratio of at least about 100 and being effective over a width of at least ½", whereby said gathering means provides improved body conformity without undue application of pressure upon the skin of the wearer, said gathering means being secured to both said backing and said facing, and said backing and said facing being unsecured to each other in the side marginal portion between the gathering means and the longitudinal side edges of the diaper, whereby said gathering means provides aesthetically pleasing ruffles at the side edges of the diaper.

24. A disposable diaper according to claim 23 wherein the gathering means are defined by an elastic member having a width dimension of at least ¾" and a width-to-thickness ratio of at least about 100 and are effective over a width of at least ¾".

25. A disposable diaper according to claim 23 wherein the gathering means are secured to the backing by at least two spaced lines of attachment and secured to the facing by at least two spaced lines of attachment and lines of attachment cooperating with one another to provide visibly distinct separate lines of simulated stitching.

26. A disposable diaper according to claim 25 wherein the gathering means are defined by an elastic member having a width dimension of at least ¾" and a width-to-thickness ratio of at least about 100 and are effective over a width of at least ¾".

* * * * *